(12) United States Patent
Kawagishi et al.

(10) Patent No.: US 8,167,807 B2
(45) Date of Patent: May 1, 2012

(54) ULTRASONIC DIAGNOSIS DEVICE, ULTRASONIC IMAGE ANALYSIS DEVICE, AND ULTRASONIC IMAGE ANALYSIS METHOD

(75) Inventors: Tetsuya Kawagishi, Nasushiobara (JP); Yasuhiko Abe, Otawara (JP); Hiroyuki Ohuchi, Otawara (JP); Katsuhisa Ishii, Osaka (JP)

(73) Assignees: Toshiba Medical Systems Corporation, Otawara-shi (JP); The Kansai Electric Power Co., Inc., Osaka (JP)

( * ) Notice: Subject to any disclaimer, the term of this patent is extended or adjusted under 35 U.S.C. 154(b) by 535 days.

(21) Appl. No.: 12/336,945

(22) Filed: Dec. 17, 2008

(65) Prior Publication Data
US 2009/0163815 A1     Jun. 25, 2009

(30) Foreign Application Priority Data

Dec. 20, 2007  (JP) ................................ 2007-329002
Oct. 2, 2008   (JP) ................................ 2008-257511

(51) Int. Cl.
*A61B 8/00* (2006.01)
(52) U.S. Cl. .................. 600/453; 600/437; 600/443
(58) Field of Classification Search .................. 600/437, 600/443, 450–458, 462, 467, 468
See application file for complete search history.

(56) References Cited

U.S. PATENT DOCUMENTS

| | | | |
|---|---|---|---|
| 7,837,625 B2 * | 11/2010 | Abe | 600/454 |
| 2006/0122512 A1 * | 6/2006 | Abe | 600/454 |
| 2009/0112088 A1 * | 4/2009 | Ohuchi et al. | 600/438 |

FOREIGN PATENT DOCUMENTS

JP  2005-130877  5/2005

* cited by examiner

*Primary Examiner* — Michael Rozanski
(74) *Attorney, Agent, or Firm* — Oblon, Spivak, McClelland, Maier & Neustadt, L.L.P.

(57) ABSTRACT

A motion parameter measuring unit two-dimensionally measures a motion parameter of a myocardial tissue by a tracking process on time-series ultrasonic image data acquired from a sample. A time phase setting unit adds a diastolic heartbeat time phase, which is set on the basis of a systole end specified by a time phase where a cardiac cavity area of the ultrasonic image data is the smallest and a diastole end specified by an R wave in an electrocardiographic waveform of the sample, relative to the systole end to time-series parameter image data generated by a parameter image data generating unit on the basis of the motion parameter. An image data extracting unit extracts parameter image data to which the diastolic heartbeat time phase closest to a desired diastolic heartbeat time phase set by an input unit is added and displays the extracted parameter image data.

27 Claims, 7 Drawing Sheets

ULTRASONIC DIAGNOSIS DEVICE, ULTRASONIC IMAGE ANALYSIS DEVICE, AND ULTRASONIC IMAGE ANALYSIS METHOD

CROSS-REFERENCE TO RELATED APPLICATIONS

This application is based upon and claims the benefit of priority from prior Japanese Patent Applications No. 2007-329002, filed Dec. 20, 2007; and No. 2008-257511, filed Oct. 2, 2008, the entire contents of both of which are incorporated herein by reference.

BACKGROUND OF THE INVENTION

1. Field of the Invention

The present invention relates to an ultrasonic diagnosis device, an ultrasonic image analysis device, and an ultrasonic image analysis method, and more particularly, to an ultrasonic diagnosis device, an ultrasonic image analysis device, and an ultrasonic image analysis method that can generate and display parameter image data based on motion parameters of myocardium and the like by analyzing ultrasonic image data collected from a sample.

2. Description of the Related Art

An ultrasonic diagnosis device radiates ultrasonic pulses generated from a vibrating element built in an ultrasonic probe into a sample, receives reflected ultrasonic waves resulting from a difference in acoustic impedance between sample tissues by the use of the vibrating element, and then displays the received ultrasonic waves on a monitor. This diagnosis method is widely used for shape diagnosis or function diagnosis of biological organs, since the method can allow real-time two-dimensional image data to easily be observed with a simple operation of bringing the ultrasonic probe into contact with a simple surface.

An ultrasonic diagnosis method of acquiring biological information by the use of ultrasonic waves reflected from tissues or globules in a biological sample has been rapidly developed with the development of two techniques of an ultrasonic pulse reflecting method and an ultrasonic Doppler method. The observation of B-mode image data or color Doppler image data obtained by the techniques is essential to today's ultrasonic image diagnosis.

In recent years, a strain imaging method of two-dimensionally observing "strains" on the basis of motion velocity information of myocardial tissues which could be acquired by analyzing ultrasonic image data such as B-mode image data was attempted.

In the strain imaging method for the function diagnosis of a heart, B-mode image data are collected in time series on the basis of received signals acquired by the scanning of ultrasonic waves on a sample and a tracking process using the pattern matching is performed on ultrasonic image data temporally adjacent to each other to measure "displacements" of parts of the myocardial tissues. Then, by calculating a two-dimensional distribution of the "strains" defined as a displacement per unit length, strain image data are generated.

There was also suggested a method of measuring the two-dimensional distribution of "strain velocity" from the spatial gradient of the motion velocity acquired by a tissue Doppler imaging (TDI) method of two-dimensionally displaying the motion velocity of the myocardial tissues by adapting the color Doppler method and temporally integrating the "strain velocity" to generate the strain image data (for example, Japanese Unexamined Patent Application Publication 2005-130877).

The time-series strain image data acquired by the use of the strain imaging method are overlapped with the ultrasonic image data such as B-mode image data used to generate the strain image data and are displayed as moving images on a monitor as a display unit.

In the recent ultrasonic diagnosis in the field of the heart, it became clear that the cardiac disorder could be early diagnosed by observing in detail parameter image data such as strain image data at a predetermined time phase of the initial diastole.

When the parameter image data at the predetermined time phase of the initial diastole are selectively observed, it was difficult to accurately observe the "strain" of the myocardial tissues at the predetermined time phase from the parameter image data continuously displayed as the moving images like the past.

Since it is necessary to use an end systole of the myocardial tissues as a reference to accurately setting the predetermined time phase, it was difficult to accurately set the predetermined time phase in the methods based on the end systole specified by R-wave timing of the electrocardiographic waveforms like the past.

BRIEF SUMMARY OF THE INVENTION

The invention is contrived in view of the above-mentioned problems and it is thus an object of the invention to provide an ultrasonic diagnosis device, an ultrasonic image analysis device, and an ultrasonic image analysis method that can allow parameter image data corresponding to a predetermined heartbeat time phase of the diastole effective for diagnosis to accurately and reliably be displayed at the time of observing the parameter image data based on motion parameters of myocardial tissues which can be acquired by analyzing ultrasonic image data.

According to an aspect of the invention, there is provided an ultrasonic diagnosis device for measuring a motion parameter of a biological tissue on the basis of time-series ultrasonic image data collected by ultrasonic scanning on a sample and generating parameter image data on the basis of the motion parameter, the ultrasonic diagnosis device including: a motion parameter measuring unit measuring a motion parameter of the biological tissue on the basis of the ultrasonic image data; a parameter image data generating unit generating time-series parameter image data on the basis of the motion parameter; a heartbeat period setting unit setting the diastole and the systole of the biological tissue; a time phase setting unit setting a diastolic heartbeat time phase relative to the systole end of the biological tissue on the respective time-series parameter image data at least in the diastole of the ultrasonic image data; a heartbeat time phase setting unit setting a desired heartbeat time phase in the diastole; an image data extracting unit extracting the parameter image data at the diastolic heartbeat time phase corresponding to the desired heartbeat time phase; and a display unit displaying the extracted parameter image data.

According to another aspect of the invention, there is provided an ultrasonic image analysis device including: an ultrasonic image data storage unit storing time-series ultrasonic image data collected by ultrasonic scanning on a sample; a motion parameter measuring unit measuring a motion parameter of a biological tissue on the basis of the ultrasonic image data; a parameter image data generating unit generating time-series parameter image data on the basis of the motion parameter; a heartbeat period setting unit setting the diastole and the systole of the biological tissue; a time phase setting unit setting a diastolic heartbeat time phase relative to the systole end of the biological tissue on the respective time-series parameter image data at least in the diastole of the ultrasonic image data; a heartbeat time phase setting unit setting a desired heartbeat time phase in the diastole; an image data extracting unit extracting the parameter image data at the diastolic heartbeat time phase corresponding to the desired heartbeat time phase; and a display unit displaying the extracted parameter image data.

According to yet another aspect of the invention, there is provided an ultrasonic image analysis method including: measuring a motion parameter of a biological tissue on the basis of the ultrasonic image data storing the time-series ultrasonic image data collected by ultrasonic scanning on a sample; generating time-series parameter image data on the basis of the motion parameter; setting the diastole and the systole of the biological tissue; setting a diastolic heartbeat time phase relative to the systole end of the biological tissue on the respective time-series parameter image data at least in the diastole of the ultrasonic image data; setting a desired heartbeat time phase in the diastole; extracting the parameter image data at the diastolic heartbeat time phase corresponding to the desired heartbeat time phase; and displaying the extracted parameter image data.

DETAILED DESCRIPTION OF THE INVENTION

Hereinafter, embodiments of the invention will be described with reference to the accompanying drawings.
First Embodiment
An ultrasonic diagnosis device according to a first embodiment of the invention to be described below transmits and receives ultrasonic waves to and from a sample to generate B-mode image data as ultrasonic image data and performs a tracking process on the ultrasonic image data to two-dimensionally or three-dimensionally measure a "strain" of a cardiac tissue as a motion parameter. In addition, the ultrasonic diagnosis device sets a diastolic heartbeat time phase based on the systole end on the basis of a systole end specified by a time phase where a cardiac cavity area of the ultrasonic image data is the minimum and a diastole end specified by an R wave in electrocardiographic waveforms of the sample measured at the same time as collecting the ultrasonic image data, and adds the diastolic heartbeat time phase to time-series parameter image data generated on the basis of the motion parameter of the ultrasonic image data. The ultrasonic diagnosis device extracts and displays from plural time-series parameter image data parameter image data at the diastolic heartbeat time phase closest to the desired diastolic heartbeat time phase set by an input unit.

Figure 1:
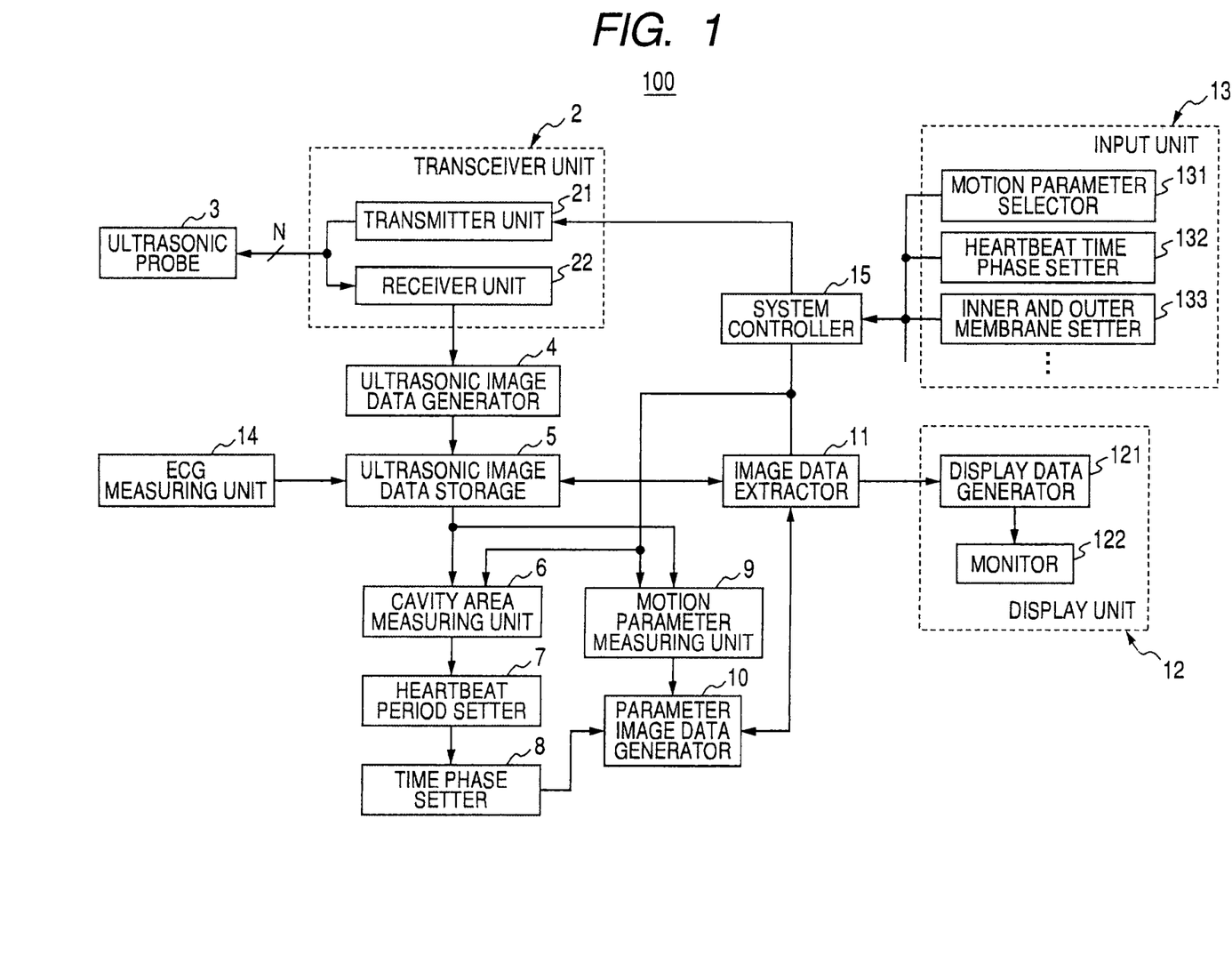
FIG. 1 is a block diagram illustrating the entire configuration of an ultrasonic diagnosis device according to a first embodiment of the invention.
Figure 2:
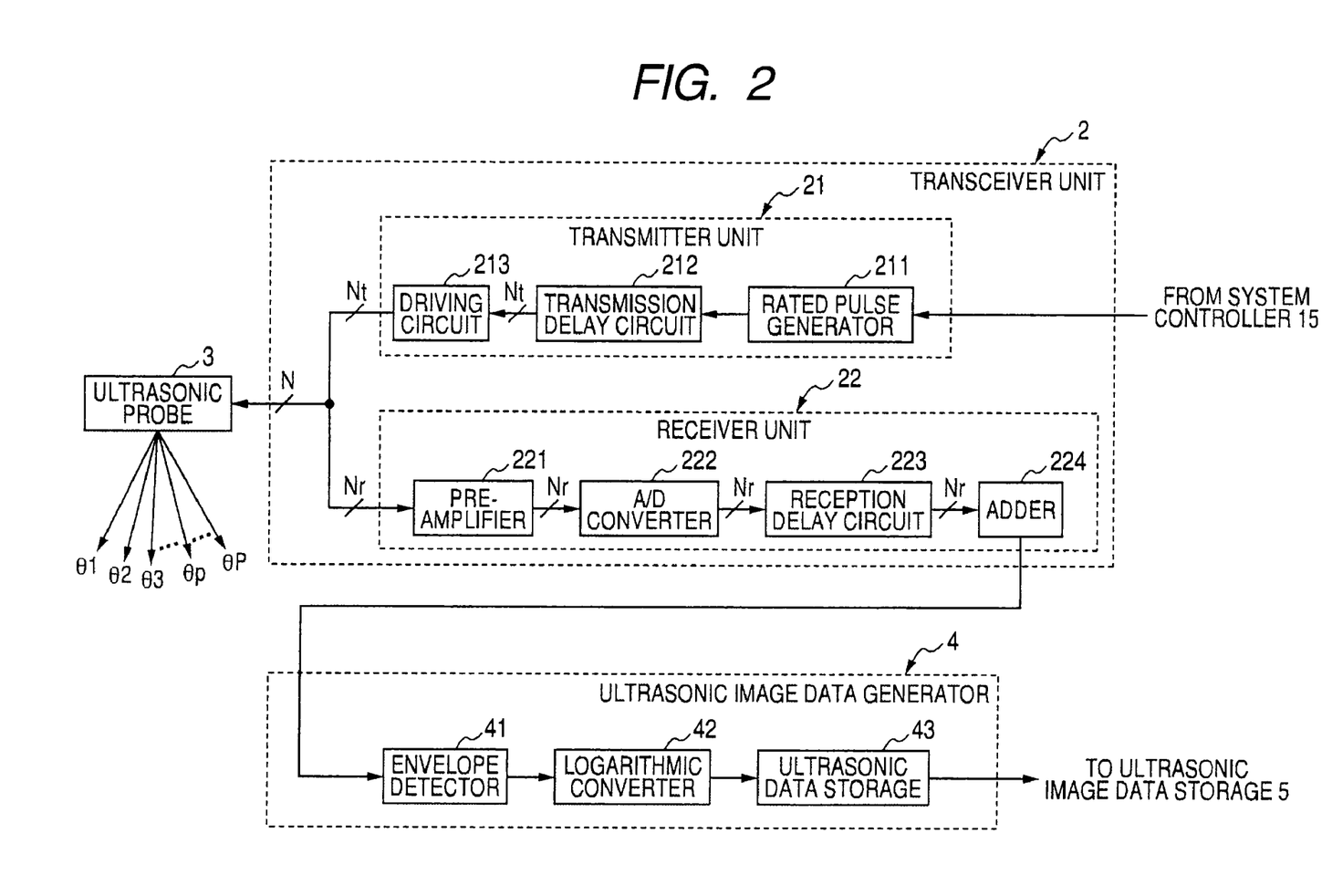
FIG. 2 is a block diagram illustrating the specific configuration of a transceiver unit and an ultrasonic image data generating unit of the ultrasonic diagnosis device according to the first embodiment.

In the below embodiment, the "strain" of the myocardial tissue is measured as the motion parameter, but the embodiment is not limited to the strain. For example, "displacement", "rotation", "torsion", "velocity", and the like may be measured as the motion parameter. A "strain rate", a "rotation rate", a "torsion rate", an "acceleration", and the like indicating temporal variations thereof may be measured.
Configuration The configuration and basic operations of the ultrasonic diagnosis device according to the first embodiment of the invention will be described now with reference to FIGS. 1 to 4. FIG. 1 is a block diagram illustrating the entire configuration of the ultrasonic diagnosis device and FIG. 2 is a block diagram illustrating the specific configuration of a transceiver unit and an ultrasonic image data generating unit of the ultrasonic diagnosis device.

The ultrasonic diagnosis device 100 shown in FIG. 1 includes an ultrasonic probe 3 in which plural vibrating elements are arranged to transmit ultrasonic pulses (transmitted ultrasonic waves) to a diagnosis target site (cardiac area) of a sample and to convert reflected ultrasonic waves (received ultrasonic waves) obtained in response to the transmission into electrical signals (received signals), a transceiver unit 2 supplying a driving signal for transmitting the ultrasonic pulses to a predetermined site of the sample to the vibrating elements and adding plural-channel received signals acquired from the vibrating elements in arranged phases, an ultrasonic image data generating unit 4 processing the added received signals to generate ultrasonic image data, an ultrasonic image data storage unit 5 adding R-wave timing information of an electrocardiographic waveform supplied from an ECG measuring unit 14 to be described later to the ultrasonic image data with a time series supplied from the ultrasonic image data generating unit 4 and storing the resultant data, a cavity area measuring unit 6 measuring a cardiac cavity area in the ultrasonic image data, a heartbeat period setting unit 7 searching the time-series ultrasonic image data for ultrasonic image data (first ultrasonic image data) having the smallest cardiac cavity area and ultrasonic image data (second ultrasonic image data) having R-wave timing information and setting the diastole and the systole of a myocardial tissue on the basis of the systole end specified by the first ultrasonic image data and the diastole end specified by the second ultrasonic image data, and a time phase setting unit 8 setting a heartbeat time phase of the diastole (hereinafter referred to as "diastolic heartbeat time phase") subsequent to the systole end on the basis of the systole end.

The ultrasonic diagnosis device 100 includes a motion parameter measuring unit 9 measuring a motion parameter in the respective ultrasonic image data read in time series from the ultrasonic image data storage unit 5, a parameter image data generating unit 10 generating parameter image data on the basis of the measured two-dimensional motion parameter, adding information on the diastolic heartbeat time phase supplied from the time phase setting unit 8 to the parameter image data, and storing the resultant information in its storage, an image data extracting unit 11 extracting the parameter image data at the diastolic heartbeat time phase closest to a desired diastolic heartbeat time phase to be described later from the plural time-series parameter image data stored in the storage of the parameter image data generating unit 10 and extracting the ultrasonic image data corresponding to the extracted parameter image data (that is, used to generate the parameter image data) from the plural ultrasonic image data stored in the ultrasonic image data storage unit 5, a display unit 12 synthesizing and displaying the extracted ultrasonic image data and the extracted parameter image data, an input unit 13 performing the selection of the motion parameter, the setting of the desired heartbeat time phase in the diastole, the setting of the inner cardiac membrane and the outer cardiac membrane on the reference ultrasonic image data selected from the plural ultrasonic image data, and the inputting of various command signals, an ECG measuring unit 14 measuring an electrocardiographic waveform (ECG) of the sample and generating R-wave timing information on the basis of R waves of the measured electrocardiographic waveform, and a system control unit 15 generally controlling the units of the ultrasonic diagnosis device 100.

The ultrasonic probe 3 has N vibrating elements not shown but arranged at its end and brings the end into contact with the sample surface to transmit and receive ultrasonic waves. The vibrating element is an electroacoustic conversion element and has a function of converting electrical pulses (driving signal) into ultrasonic pulses (transmitted ultrasonic waves) at the time of transmission and converting reflected ultrasonic waves (received ultrasonic waves) into electrical signals at the time of reception. The vibrating elements are connected to the transceiver unit 2 through an N-channel multi-core cable not shown. In this embodiment, a sector-scanning ultrasonic probe 3 having N vibrating elements is described, but an ultrasonic probe corresponding to linear scanning or convex scanning may be employed.

The transceiver unit 2 shown in FIG. 2 includes a transmitter unit 21 supplying the driving signal to the vibrating elements of the ultrasonic probe 3 and a receiver unit 22 arranged-phase adding the received signal acquired from the vibrating elements.

The transmitter unit 21 includes a rated pulse generator 211, a transmission delay circuit 212, and a driving circuit 213. The rated pulse generator 211 generates rated pulses for determining the repetition period of the transmitted ultrasonic waves by dividing a reference signal supplied from the system control unit 15. The transmission delay circuit 212 includes independent delay circuits of the same number as Nt vibrating elements used for transmission and gives a concentrating delay time for concentrating the transmitted ultrasonic waves at a predetermined depth and an inclining delay time for transmitting the transmitted ultrasonic waves in a predetermine direction θp to the rated pulses supplied from the rated pulse generator 211. The driving circuit 213 includes independent driving circuits of the same number as the transmission delay circuits 212 and generates the driving signal on the basis of the rated pulses to which the delay time is given by the transmission delay circuit 212. The Nt (Nt≦N) vibrating elements selected for transmission from the N vibrating elements built in the ultrasonic probe 3 are driven by the driving signal and the transmitted ultrasonic waves are radiated to the inside of the sample.

On the other hand, the receiver unit 22 includes an Nr-channel pre-amplifier 221 corresponding to the Nr (Nr≦N) vibrating elements selected for reception from the N vibrating elements built in the ultrasonic probe 3, an A/D converter 222, a reception delay circuit 223, and an adder 224. The Nr-channel received signal supplied from the receiving vibrating elements through the pre-amplifier 221 is converted into a digital signal by the A/D converter 222 and then is sent to the reception delay circuit 223.

The reception delay circuit 223 gives a concentrating delay time for concentrating the received ultrasonic waves from the predetermined depth and an inclining delay time for setting the reception directivity in the predetermined direction θp to the Nr-channel received signals output from the A/D converter 222. The adder 224 adds the received signals from the reception delay circuit 223. That is, the received signals in the predetermined direction θp are added in arranged phases by the reception delay circuit 223 and the adder 224. The reception delay circuit 223 and the adder 224 enable the so-called parallel simultaneous reception method of simultaneously forming the reception directivity in plural directions by controlling the delay time and thus the time for scanning is greatly reduced by employing the parallel simultaneous reception method.

The ultrasonic image data generating unit 4 has a function of generating, for example, B-mode image data as the ultrasonic image data, and includes an envelope detector 41, an algebraic converter 42, and an ultrasonic data storage 43. The envelope detector 41 detects an envelope of the added received signals supplied from the adder 224 of the receiver unit 22. The received signals of which the envelope is detected are algebraically converted in amplitude by the algebraic converter 42 and B-mode data in the predetermined direction θp are generated. With the transmission and reception of ultrasonic waves in the transmission and reception directions θp (θp=θ1 to θp), the B-mode data sequentially supplied from the algebraic converter 42 are stored in the ultrasonic data storage 43 to correspond to the transmission and reception directions and then the ultrasonic image data (B-mode image data) are generated. The order of the envelope detector 41 and the algebraic converter 42 may be changed.

Referring to FIG. 1 again, the ultrasonic image data storage unit 5 adds the R-wave timing information of the electrocardiographic waveform supplied from the ECG measuring unit 14 to the time-series ultrasonic image data corresponding to several heartbeat periods and supplied from the ultrasonic image data generating unit 4 and stores the added ultrasonic image data. That is, the R-wave timing information is added to the ultrasonic image data (hereinafter, referred to as reference ultrasonic image data) generated by the ultrasonic image data generating unit 4 at the time of detecting the R wave of the electrocardiographic waveform.

The cavity area measuring unit 6 reads the plural time-series ultrasonic image data stored in the ultrasonic image data storage unit 5, performs a tracking process based on the inner cardiac membrane set on the myocardial tissue in the reference ultrasonic image data selected from the read ultrasonic image data by the input unit 13 on the ultrasonic image data, which corresponds to one heartbeat period, subsequent to the reference ultrasonic image data, and detects the inner cardiac membrane in the ultrasonic image data. The cavity area measuring unit measures the cardiac cavity area surround with the inner cardiac membrane in the ultrasonic image data and supplies the measurement result to the heartbeat period setting unit 7 along with identification information on the ultrasonic image data (hereinafter, referred to as image data identification information) and the R-wave timing information.

Then, the heartbeat period setting unit 7 specifies the systole end by retrieving the ultrasonic image data (first ultrasonic image data) in which the cardiac cavity area is the minimum on the basis of the information supplied from the cavity area measuring unit 6 and specifies the diastole end by retrieving the reference ultrasonic image data (second ultrasonic image data) to which the R-wave timing information is added. Then, the heartbeat period setting unit sets the diastole and the systole of the myocardial tissue on the basis of the systole end and the diastole end.

On the other hand, the time phase setting unit 8 includes a memory circuit not shown and sets the heartbeat time phase (diastolic heartbeat time phase) based on the systole end on the time-series ultrasonic image data collected in the diastole. However, the diastolic heartbeat time phase is set by a ratio (for example, a ratio of 30% of the period T, T/3 when the period from the systole end to the diastole end is T) based on the period from the systole end to the diastole end, and the diastolic heartbeat time phase set at that time is stored in the memory circuit to correspond to the image data identification information on the ultrasonic image data.

The motion parameter measuring unit 9 includes a sampling point setting unit and a tracking processing unit not shown. The sampling point setting unit reads the plural time-series ultrasonic image data stored in the ultrasonic image data storage unit 5 and sets plural sampling points with a predetermined interval for the myocardial tissue surrounded with the inner cardiac membrane and the outer cardiac membrane set data by the input unit 13 on the reference ultrasonic image data selected from the read ultrasonic image. On the other hand, the tracking processing unit performs a tracking process using the pattern matching based on the sampling points set on the reference ultrasonic image data, measures the "displacement" of the parts of the myocardial tissue, and measures the "strain" defined by displacement per unit length as the motion parameter.

The parameter image data generating unit 10 generates plural time-series parameter image data on the basis of the two-dimensional motion parameter measured by the motion parameter measuring unit 9. Subsequently, the parameter image data generating unit reads the diastolic heartbeat time phase stored in the memory circuit of the time phase setting unit 8 along with the image data identification information, adds the diastolic heartbeat time phase corresponding to the image data identification information of the ultrasonic image data used for generating the parameter image data to the parameter image data, and stores the resultant data in its memory circuit. That is, the time-series parameter image data in the diastole in which the diastolic heartbeat time phase based on the systole end is set are stored in the memory circuit of the parameter image data generating unit 10.

On the other hand, the image data extracting unit 11 extracts the ultrasonic image data having the R-wave timing information as the reference ultrasonic image data from the time-series ultrasonic image data stored in the ultrasonic image data storage unit 5. The image data extracting unit extracts the parameter image data to which the information on the diastolic heartbeat time phase closest to the desired heartbeat time phase from the plural parameter image data stored in the parameter image data generating unit 10 on the basis of the information on the desired heartbeat time phase of the diastole supplied from the input unit 13 through the system control unit 15, and extracts the ultrasonic image data used for generating the parameter image data from the plural ultrasonic image data stored in the ultrasonic image data storage unit 5.

The display unit 12 includes a display data generator 121 and a monitor 122. The display data generator 121 generates display data by performing a predetermined conversion process on the reference ultrasonic image data supplied from the image data extracting unit 11. The display unit performs a predetermined conversion process and a synthesis process on the parameter image data and the ultrasonic image data at the diastolic heartbeat time phase, which is closest to the desired diastolic heartbeat time phase, supplied from the image data extracting unit 11 and adds sample information or electrocardiographic waveforms thereto as needed, to generate display data. The display unit then displays the display data on the monitor 122.

The input unit 13 has an input device or a display panel such as a keyboard, a track ball, a mouse, a selection button, and an input button on an operation panel and includes a motion parameter selector 131 selecting the motion parameter, a heartbeat time phase setting unit 132 setting the desired diastolic heartbeat time phase, and an inner and outer membrane setting unit 133 setting the inner cardiac membrane and the outer cardiac membrane on the myocardial tissue of the reference ultrasonic image data. The inputting of the sample information, the setting of generation conditions or display conditions of various image data, and the inputting of various command signals are performed by the use of the display panel or the input device.

Figure 3:
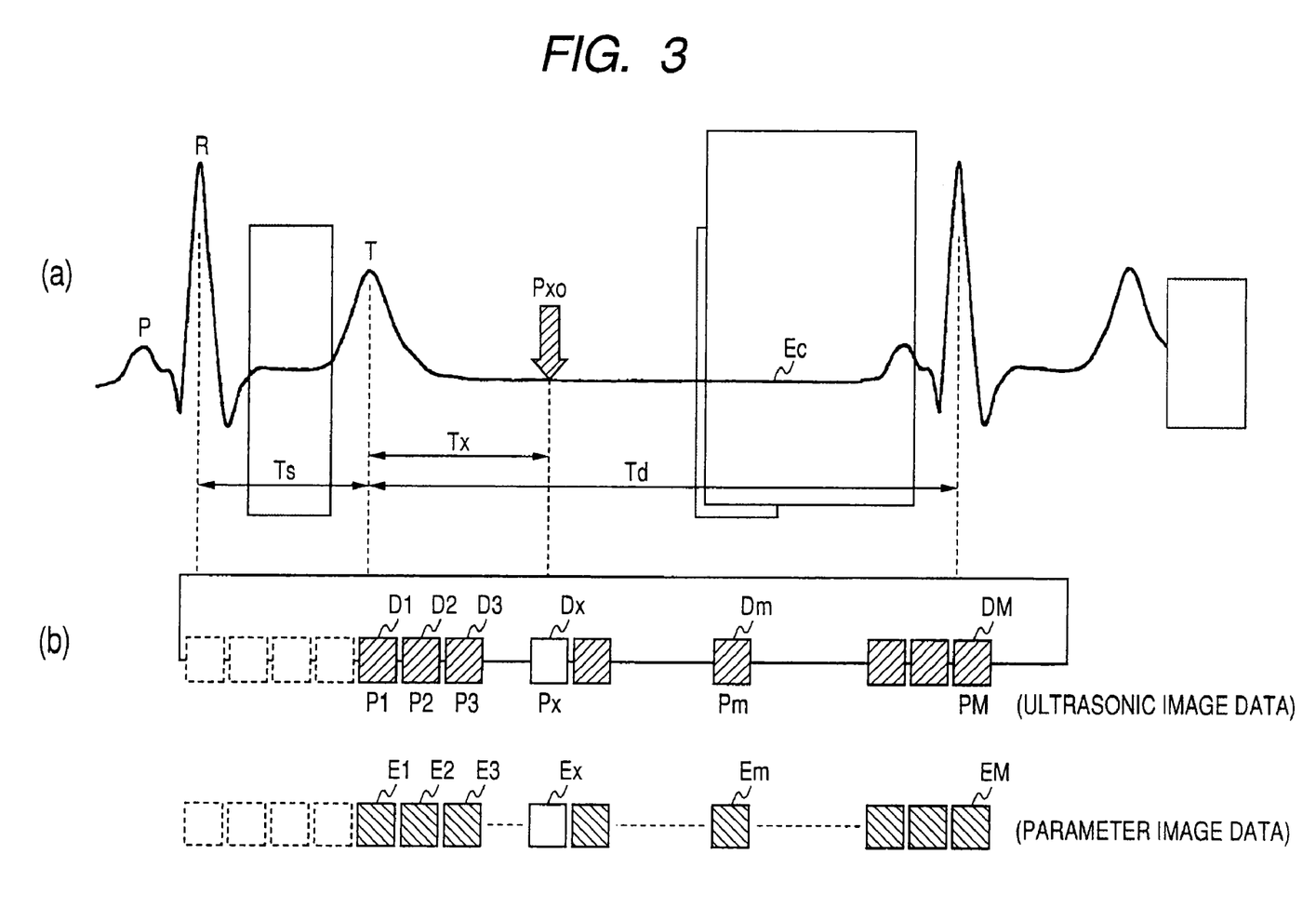
FIG. 3 is a diagram illustrating the diastole and the systole of a myocardial tissue set by a heartbeat period setting unit and a desired heartbeat time phase of the diastole set by a heartbeat time phase setting unit of the ultrasonic diagnosis device according to the first embodiment.

FIG. 3 shows the diastole and the systole of the myocardial tissue set by the heartbeat period setting unit 7 and the desired diastolic heartbeat time phase set by the heartbeat time phase setting unit 132.

That is, in FIG. 3(*a*), the systole of the myocardial tissue corresponds to the period Ts from the R wave to the T wave in the electrocardiographic waveform Ec of the sample measured by the ECG measuring unit 14 and the diastole corresponds to the period Td from the T wave to the R wave in the electrocardiographic waveform Ec. As described above, a cardiac disorder can be early diagnosed by measuring the motion parameter of the myocardial tissue at the desired diastolic heartbeat time phase Pxo (Pxo=Tx/Td×100(%)) in a predetermined time Tx after the systole end. However, it is not easy to detect the T wave from the electrocardiographic waveform Ec of the sample having the cardiac disorder to specify the systole end, and thus a method of specifying the systole end by detecting the time phase at which the cardiac cavity area shown in the ultrasonic image data is the minimum as described above is suitable.

On the other hand, FIG. 3(*b*) schematically shows the M time-series ultrasonic image data D1 to DM at the diastole extracted from the time-series ultrasonic image data generated with the measurement of the electrocardiographic waveform Ec, the diastolic heartbeat time phases P1 to PM set on the ultrasonic image data D1 to DM by the time phase setting unit 8, and the parameter image data E1 to EM generated on the basis of the ultrasonic image data D1 to DM. That is, the diastolic heartbeat time phase P1 is set on the ultrasonic image data D1 generated at the systole end shown by the T wave of the electrocardiographic waveform Ec and the parameter image data E1 acquired by the tracking process based on the ultrasonic image data D1, and the diastolic heartbeat time phases P2 to PM are set on the ultrasonic image data D2 to DM generated with a predetermined interval subsequent to the ultrasonic image data D1 and the parameter image data E2 to EM generated on the basis of the image data.

When the desired diastolic heartbeat time phase Pxo is set by the heartbeat time phase setting unit 132 of the input unit 13, the image data extracting unit 11 having received the setting information through the system control unit 15 extracts the parameter image data Ex and the ultrasonic image data Dx at the diastolic heartbeat time phase Px corresponding to the desired heartbeat time phase Pxo (that is, closest to the desired heartbeat time phase Pxo) and displays the extracted data on the display unit 12.

In the above-mentioned method, the diastolic heartbeat time phases P1 to PM are set on the parameter image data E1 to EM generated in advance and the parameter image data Ex having the diastolic heartbeat time phase Px closest to the desired heartbeat time phase Pxo is extracted. However, the parameter image data Ex may be generated directly on the basis of the ultrasonic image data Dx at the diastolic heartbeat time phase Px closest to the desired heartbeat time phase Pxo.

Figure 4:
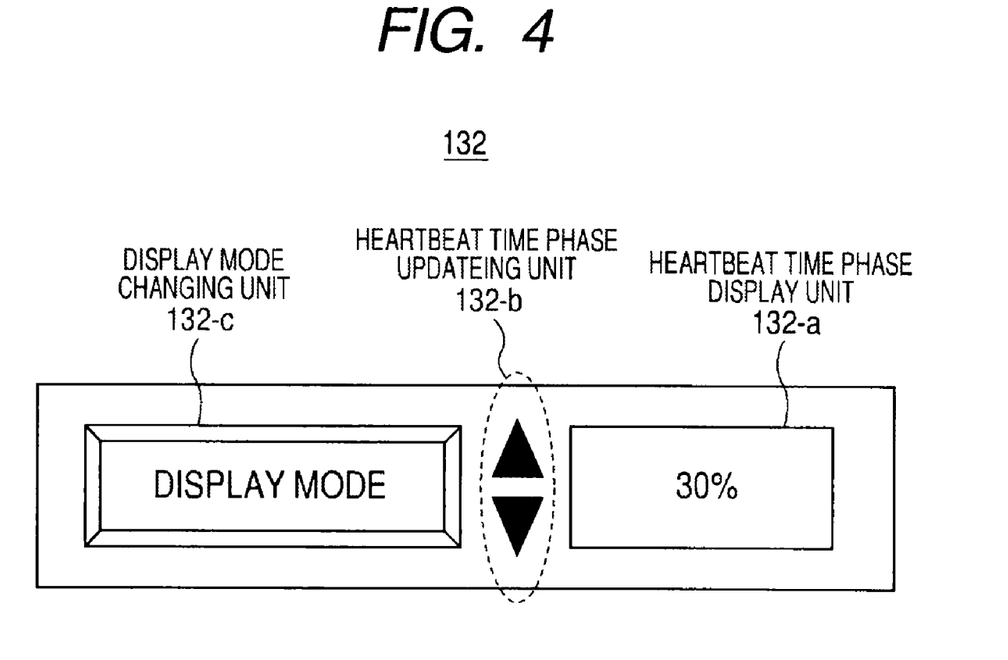
FIG. 4 is a diagram illustrating an example of the heartbeat time phase setting unit of the ultrasonic diagnosis device according to the first embodiment.

A specific example of the heartbeat time phase setting unit 132 disposed in the input unit 13 will be described with reference to FIG. 4. The heartbeat time phase setting unit 132 includes a heartbeat time phase display 132-*a* displaying the desired heartbeat time phase Pxo in the diastole in the ratio (%) based on the period from the systole end to the diastole end, a heartbeat time phase updating section 132-*b* updating the desired heartbeat time phase by changing the desired heartbeat time phase displayed in the heartbeat time phase display 132-*a*, and a display mode switching section 132-*c* switching a fixed display mode in which one parameter image data corresponding to the desired diastolic heartbeat time phase is displayed and an update display mode in which plural parameter image data corresponding to the desired heartbeat time phases in the plural heartbeat periods are sequentially updated and displayed. By operating the heartbeat time phase updating section 132-*b* while observing the desired heartbeat time phase displayed on the heartbeat time phase display 132-*a*, the period Tx from the systole end to the desired heartbeat time phase Pxo shown in FIG. 3(*a*) is set to a desired ratio (a predetermined ratio between 30% to 34%, for example, about 33% corresponding to ⅓ of the diastole) with respect to the diastole Td.

Referring to FIG. 1 again, the ECG measuring unit 14 has a function of generating the R-wave timing information on the basis of the R wave detected from the electrocardiographic waveform of the sample and includes a measuring electrode disposed on the sample surface to measure the electrocardiographic waveform, an amplification circuit amplifying the electrocardiographic waveform measured by the measuring electrode to a predetermined amplitude, an A/D converter converting the amplified electrocardiographic waveform into a digital signal, and an R-wave detector setting a predetermined threshold value in the electrocardiographic waveform converted into the digital signal to detect the R wave, which are not shown.

The system control unit 15 includes a CPU and a memory circuit not shown and various information input, set, and selected by the input unit 13 is stored in the memory circuit. The CPU generally controls the units of the ultrasonic diagnosis device 100 on the basis of the information input from the input unit 13 or the information stored in advance in the memory circuit, and generates or displays the ultrasonic image data and the parameter image data.

Procedure of Generating and Displaying Parameter Image Data

Then, the procedure of generating and displaying the parameter image data according to this embodiment will be described with reference to the flowchart of FIG. 5.

Before generating the parameter image data, an operator of the ultrasonic diagnosis device 100 inputs the sample information by the use of the input unit 13 and then selects the "strain" of the myocardial tissue as the motion parameter by the use of the motion parameter selector 131. The operator initializes the generation conditions of the ultrasonic image data and the parameter image data or display conditions of the image data and mounts the measuring electrode of the ECG measuring unit 14 at a predetermined site of the sample (step S1 of FIG. 5).

When the initialization is ended, the operator inputs a command for generating the ultrasonic image data by the use of the input unit 13 in a state where the end of the ultrasonic probe 3 is fixed to the sample surface. When the command is supplied to the system control unit 15, the transmission and reception of the ultrasonic waves for generating the time-series ultrasonic image data is started.

That is, the rated pulse generator 211 of the transceiver unit 2 shown in FIG. 2 generates the rated pulses for determining the repetition period of the ultrasonic pulses radiated into the sample by dividing a reference signal supplied from the system control unit 15 and supplies the rated pulses to the transmission delay circuit 212.

The transmission delay circuit 212 gives the concentrating delay time for concentrating the ultrasonic waves at a predetermined depth and the inclining delay time for transmitting the ultrasonic waves in the first transmission and reception direction θ1 to the rated pulses and supplies the rated pulses to the driving circuit 213. The driving circuit 213 supplies the driving signal generated on the basis of the rated pulses to the Nt transmitting vibrating elements in the ultrasonic probe 3 through a cable not shown and radiates the ultrasonic pulses in the direction θ1 of the sample.

A part of the ultrasonic pulses radiated to the sample are reflected by the boundary of the heart or the myocardial tissue having different acoustic impedance and the reflected ultrasonic waves (received ultrasonic waves) are converted into Nt-channel electrical signals (received signals) by the Nt receiving vibrating elements of the ultrasonic probe 3. The received signals are amplified to a predetermined magnitude by the pre-amplifier 221 of the receiver unit 22 and are converted into digital signals by the A/D converter 222. A predetermined delay time is given thereto by the reception delay circuit 223 and the resultant signals are synthesized (added in arranged phases) by the adder 224. At this time, the reception delay circuit 223 sets the concentrating delay time for concentrating the reflected ultrasonic waves from the predetermined depth and the inclining delay time for giving the strong reception directivity in the transmission and reception direction θ1 to the reflected ultrasonic waves on the basis of the control signal from the system control unit 15.

The envelope detector 41 and the algebraic converter 42 of the ultrasonic image data generating unit 4 perform the enveloped detection and the algebraic conversion on the received signals bound into one channel by the arranged-phase addition of the adder 224 to generate the B mode data. The resultant B mode data are stored in the ultrasonic data storage 43.

The system control unit 15 transmits and receives the ultrasonic waves in the transmission and reception directions θ2 to θp in the same order. The acquired B mode data are also stored in the ultrasonic data storage 43. That is, the ultrasonic data storage 43 sequentially stores the B mode data acquired by the transmission and reception of the ultrasonic waves in the transmission and reception directions θ1 to θp to generate the B-mode image data corresponding to one frame as the ultrasonic image data and the generated ultrasonic image data and the image data identification information are stored in the ultrasonic image data storage unit 5.

By repeating the above-mentioned procedure, the ultrasonic image data corresponding to several heartbeat periods are generated in time series and the generated ultrasonic image data are sequentially stored in the ultrasonic image data storage unit 5 using the image data identification information as the incidental information.

On the other hand, the ECG measuring unit 14 detects the R wave by setting a predetermined threshold value to the electrocardiographic waveform detected by the measuring electrode and converted by the A/D converter in the A/D conversion manner. The R-wave timing information indicating the timing when the R wave is detected is sent to the ultrasonic image data storage unit 5 and is added to the ultrasonic image data supplied from the ultrasonic image data generating unit 4 to the ultrasonic image data storage unit 5. That is, the B-mode image data generated at the heartbeat time phase of the R wave are stored in the ultrasonic image data storage unit 5 using the R-wave timing information and the image data identification information as the incidental information (step S2 of FIG. 5).

When the generation and storage of the time-series ultrasonic image data (B-mode image data) on the sample are ended, the image data extracting unit 11 extracts the ultrasonic image data having the R-wave timing information as the reference ultrasonic image data from the time-series ultrasonic image data stored in the ultrasonic image data storage unit 5 and displays the extracted ultrasonic image data on the monitor 122 of the display unit 12. The operator having observed the reference ultrasonic image data displayed on the display unit 12 sets the inner cardiac membrane and the outer cardiac membrane on the myocardial tissue of the reference ultrasonic image data by the use of the inner and outer membrane setting unit 133 of the input unit 13 (step S3 of FIG. 5).

Then, the cavity area measuring unit 6 reads the plural time-series ultrasonic image data stored in the ultrasonic image data storage unit 5 and performs the tracking process based on the inner cardiac membrane set by the use of the input unit 13 on the myocardial tissue of the reference ultrasonic image data selected from the ultrasonic image data on the ultrasonic image data corresponding to one heartbeat period subsequent to the reference ultrasonic image data, thereby detecting the inner cardiac membrane in the ultrasonic image data. Then, the cavity area measuring unit measures the cardiac cavity area surrounded with the inner cardiac membrane with respect to the respective ultrasonic image data and supplies the measurement result to the heartbeat period setting unit 7 along with the image data identification information and the R-wave timing information (step S4 of FIG. 5).

On the other hand, the heartbeat period setting unit 7 specifies the systole end by retrieving the ultrasonic image data (first ultrasonic image data) in which the cardiac cavity area is the minimum on the basis of the information supplied from the cavity area measuring unit 6, and specifies the diastole end by retrieving the ultrasonic image data (second ultrasonic image data) having the R-wave timing information. Then, the heartbeat period setting unit sets the diastole and the systole of the myocardial tissue on the basis of the systole end and the diastole end (step S5 of FIG. 5).

Figure 5:
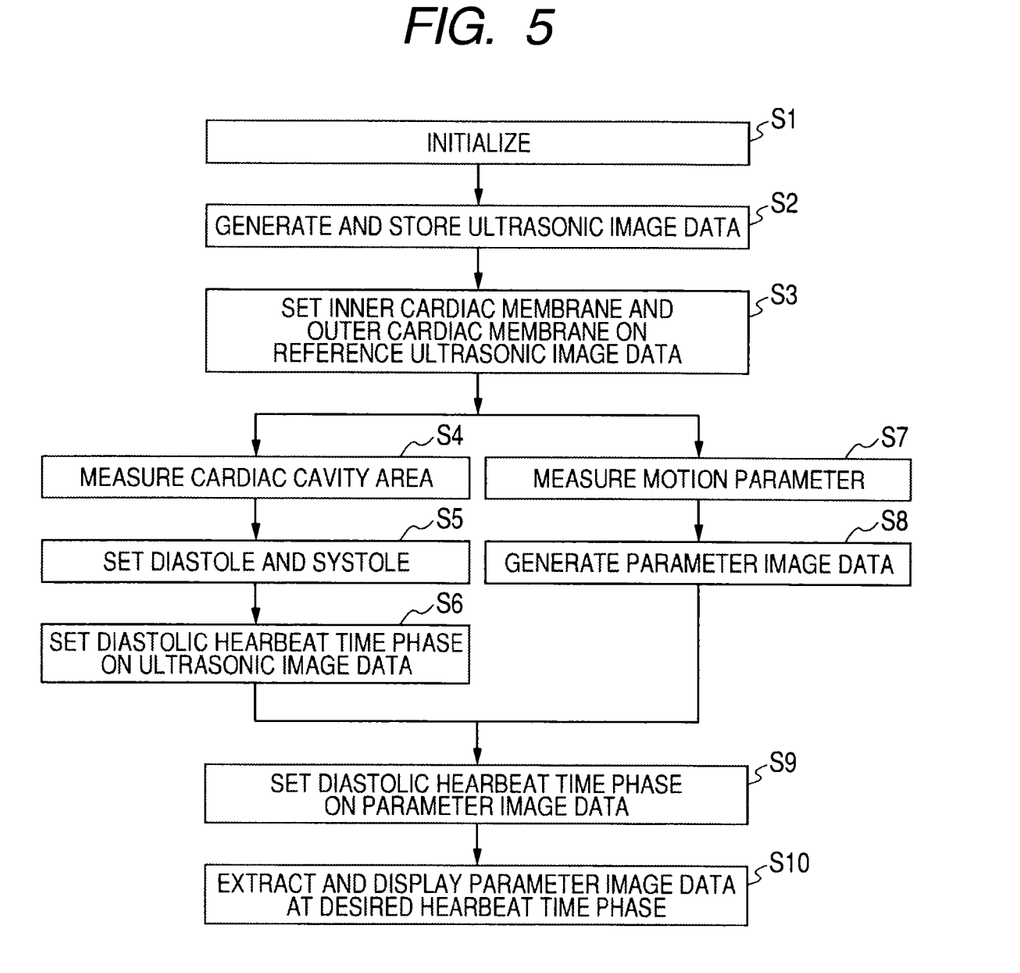
FIG. 5 is a flowchart illustrating a procedure of generating and displaying parameter image data in the ultrasonic diagnosis device according to the first embodiment.

The time phase setting unit 8 sets the diastolic heartbeat time phase based on the systole end on the respective time-series ultrasonic image data collected at the diastole and the set diastolic heartbeat time phase is stored in its memory circuit to correspond to the image data identification information of the ultrasonic image data (step S6 of FIG. 5).

The sampling point setting unit of the motion parameter measuring unit 9 reads the plural time-series ultrasonic image data stored in the ultrasonic image data storage unit 5 and sets plural sampling points with a predetermined interval on the myocardial tissue surrounded with the inner cardiac membrane and the outer cardiac membrane set on the reference ultrasonic image data selected from the read ultrasonic image data by the input unit 13. On the other hand, the tracking processor of the motion parameter measuring unit 9 performs the tracking process using the pattern matching based on the sampling points set on the reference ultrasonic image data to measure the "displacements" of the parts of the myocardial tissue and measure the "strain" defined by the displacement per unit length as the motion parameter (step S7 of FIG. 5).

Then, the parameter image data generating unit 10 generates plural time-series parameter image data on the basis of the motion parameter two-dimensionally measured by the motion parameter measuring unit 9 (step S8 of FIG. 5). Then, the parameter image data generating unit sets, for example, the 33% heartbeat time phase (the heartbeat time phase corresponding to about ⅓ of the diastole) as the desired diastolic heartbeat time phase by the use of the heartbeat time phase setting unit 132 of the input unit 13, reads the diastolic heartbeat time phase stored in the memory circuit of the time phase setting unit 8 along with the image data identification information, and sets the diastolic heartbeat time phase corresponding to the image data identification information of the ultrasonic image data used for generating the parameter image data on the parameter image data. The parameter image data generating unit stores the parameter image data with the information on the diastolic heartbeat time phase added thereto in the memory circuit thereof (step S9 of FIG. 5).

When the parameter image data storage in which the diastolic heartbeat time phase is set are completed, the image data extracting unit 11 extracts the parameter image data to which the information on the diastolic heartbeat time phase closest to the desired heartbeat time phase is added from the plural parameter image data stored in the parameter image data storage unit 10 on the basis of the desired diastolic heartbeat time phase supplied from the heartbeat time phase setting unit 132 of the input unit 13 through the system control unit 15 and extracts the ultrasonic image data corresponding to the extracted parameter image data from the plural ultrasonic image data stored in the ultrasonic image data storage unit 5.

The display data generator 121 of the display unit 12 performs the conversion process and the synthesis process on the parameter image data and the ultrasonic image data at the diastolic heartbeat time phase closest to the desired heartbeat time phase and supplied from the image data extracting unit 11 and adds the sample information or the electrocardiographic waveform thereto as needed, to generate the display data. The acquired display data is displayed on the monitor 122 (step S10 of FIG. 5). Upon the display, the parameter values may be averaged and displayed every segment, which is recommended in the American Society of Echocardiography (ASE), the American Heart Association (AHA), and the like.

According to the first embodiment of the invention, by observing the parameter image data based on the motion parameter of the myocardial tissue acquired by analyzing the ultrasonic image data, it is possible to accurately and reliably display the parameter image data at the diastolic heartbeat time phase closest to the desired diastolic heartbeat time phase effective for diagnosis. Accordingly, it is possible to improve the diagnosis efficiency and the diagnosis precision and to reduce the operator's burden.

Particularly, in this embodiment, since the systole end of the myocardial tissue is specified on the basis of the ultrasonic image data in which the cardiac cavity area is the minimum and which is selected from the time-series ultrasonic image data, it is possible to accurately set the desired diastolic heartbeat time phase based on the systole end without depending on the detection of the T wave in the electrocardiographic waveform.

Since the desired diastolic heartbeat time phase is set by the % heartbeat time phase based on the diastole, it is possible to easily set the heartbeat time phase effective for diagnosis even when the heartbeat period varies person by person.

Second Embodiment

A second embodiment of the invention will be described. An ultrasonic image analysis device according to the second embodiment of the invention performs a tracking process on time-series ultrasonic image data collected in advance in a state where the R-wave timing information based on the electrocardiographic waveform of a sample is added thereto and two-dimensionally measures a motion parameter of a myocardial tissue. On the other hand, the ultrasonic image analysis device sets a diastolic heartbeat time phase based on the systole end on the basis of the systole end specified by the time phase at which the cardiac cavity area of the ultrasonic image data is the minimum and the diastole end specified by the R-wave timing information added to the ultrasonic image data, and adds the diastolic heartbeat time phase to the respective time-series parameter image data generated on the basis of the motion parameter of the ultrasonic image data. The ultrasonic image analysis device extracts the parameter image data at the diastolic heartbeat time phase closest to the desired diastolic heartbeat time phase set by the use of the input unit from the plural time-series parameter image data and displays the extracted parameter image data.

Configuration

The configuration of the ultrasonic image analysis device according to the second embodiment of the invention will be described with reference to FIG. 6.

Figure 6:
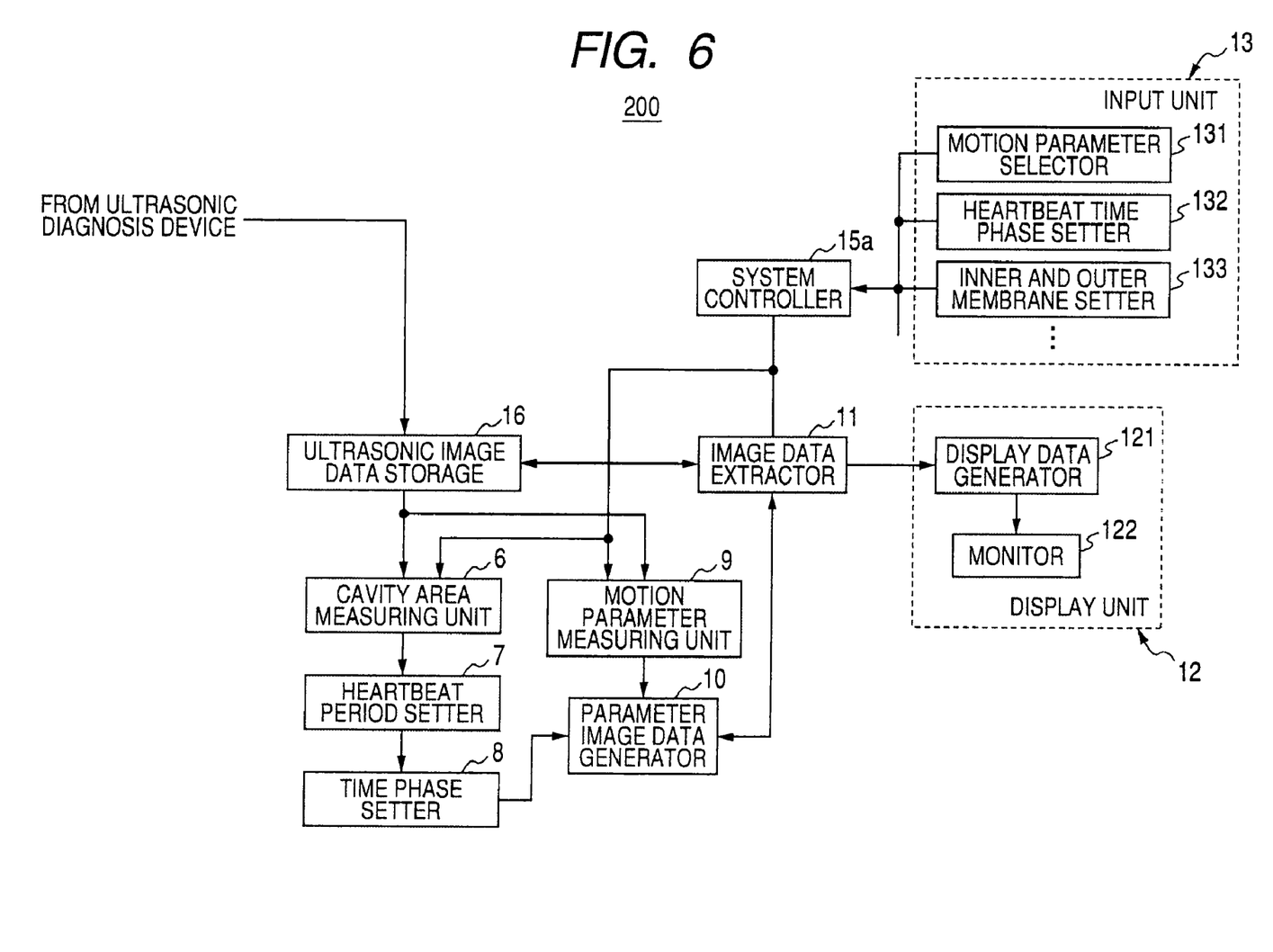
FIG. 6 is a block diagram illustrating the entire configuration of an ultrasonic image analysis device according to a second embodiment of the invention.

FIG. 6 is a block diagram illustrating the entire configuration of the ultrasonic image analysis device according to this embodiment. The units having the same configurations and functions as the units of the ultrasonic diagnosis device 100 according to the first embodiment shown in FIG. 1 are denoted by the same reference numerals and detailed description thereof is omitted.

That is, the ultrasonic image analysis device 200 shown in FIG. 6 includes an ultrasonic image data storage unit 16 storing plural time-series ultrasonic image data supplied from an independent ultrasonic diagnosis device through a network or a storage medium and R-wave timing information of an electrocardiographic waveform added to the ultrasonic image data, a cavity area measuring unit 6 measuring a cardiac cavity area in the ultrasonic image data, a heartbeat period setting unit 7 retrieving the ultrasonic image data (first ultrasonic image data) having the minimum cardiac cavity area and the ultrasonic image data (second ultrasonic image data) having the R-wave timing information from the time-series ultrasonic image data and setting the diastole and the systole of the myocardial tissue on the basis of the systole end specified by the first ultrasonic image data and the diastole end specified by the second ultrasonic image data, and a time phase setting unit 8 setting the heartbeat time phase of the diastole (diastolic heartbeat time phase) subsequent to the systole end.

The ultrasonic image analysis device 200 includes a motion parameter measuring unit 9 measuring the motion parameter of the myocardial tissue for the respective ultrasonic image data read in time series from the ultrasonic image data storage unit 16, a parameter image data setting unit 10 generating the parameter image data on the basis of the measured two-dimensional motion parameter, adding information on the diastolic heartbeat time phase supplied from the time phase setting unit 8 to the parameter image data, and storing the resultant data in its storage, an image data extracting unit 11 extracting the parameter image data at the diastolic heartbeat time phase closest to the desired diastolic heartbeat time phase from the plural time-series parameter image data stored in the storage of the parameter image data generating unit 10 and extracting the ultrasonic image data corresponding to the extracted parameter image data from the plural ultrasonic image data stored in the ultrasonic image data storage unit 5, a display unit 12 synthesizing and displaying the extracted ultrasonic image data and the extracted parameter image data, an input unit 13 performing the selection of the motion parameter, the setting of the desired heartbeat time phase in the diastole, the setting of the inner and outer cardiac membranes on the reference ultrasonic image data selected from the plural ultrasonic image data, and the inputting of various command signals, and a system control unit 15a generally controlling the units of the ultrasonic image analysis device 200.

Procedure of Generating and Displaying Parameter Image Data

Figure 7:
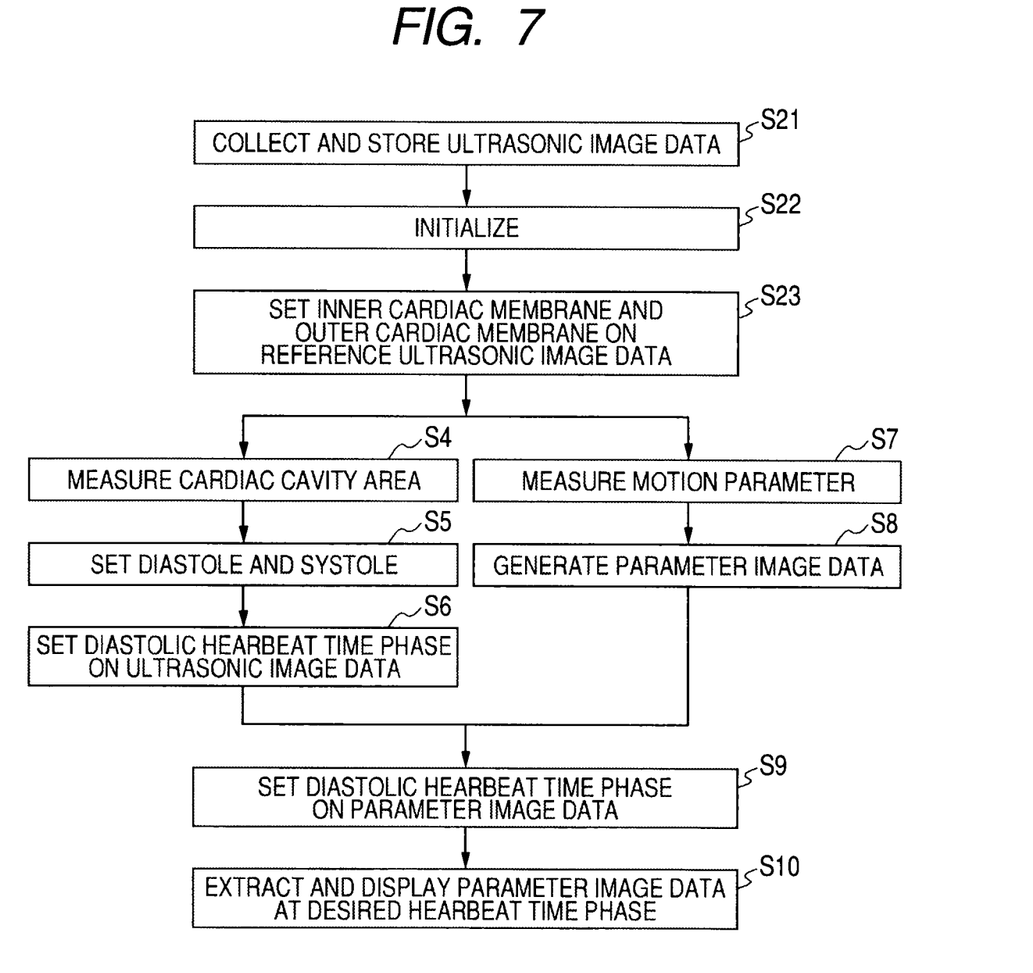
FIG. 7 is a flowchart illustrating a procedure of generating and displaying parameter image data in the ultrasonic image analysis device according to the second embodiment.

A procedure of generating and displaying the parameter image data according to this embodiment will be described with reference to the flowchart shown in FIG. 7. In FIG. 7, the same processes as the procedure of generating and displaying the parameter image data according to the first embodiment shown in FIG. 5 are denoted by the same reference numerals and signs and detailed description thereof is omitted.

Before generating the parameter image data, the plural time-series ultrasonic image data collected by an independent ultrasonic diagnosis device and the R-wave timing information based on the electrocardiographic waveform added to the ultrasonic image data are stored in the ultrasonic image data storage unit 16 of the ultrasonic image analysis device 200 through a network or a storage medium (step S21 of FIG. 7).

An operator of the ultrasonic image analysis device 200 inputs the sample information by the use of the input unit 13, selects the motion parameter suitable for diagnosis by the use of the motion parameter selector 131, and initializes the generation conditions of the parameter image data or the display conditions of the ultrasonic image data and the parameter image data (step S22 of FIG. 7).

When the initialization is ended, the operator inputs a command for starting generating the parameter image data by the use of the input unit 13. By supplying the command signal to the system control unit 15a, the generation of the time-series parameter image data is started.

That is, the image data extracting unit 11 extracts the ultrasonic image data having the R-wave timing information from the time-series ultrasonic image data stored in the ultrasonic image data storage unit 16 as the reference ultrasonic image data and displays the extracted ultrasonic image data on the monitor 122 of the display unit 12. The operator observing the reference ultrasonic image data displayed on the display unit 12 sets the inner cardiac membrane and the outer cardiac membrane on the myocardial tissue of the reference ultrasonic image data by the use of the inner and outer membrane setting unit 133 of the input unit 13 (step S23 of FIG. 7).

Then, the diastolic heartbeat time phase is set on the ultrasonic image data by the processes of steps S4 to S6 of FIG. 7 and the time-series parameter image data based on the ultrasonic image data are generated by the processes of steps S7 to S8 of FIG. 7. In step S9 of FIG. 7, the diastolic heartbeat time phase of the ultrasonic image data used for generating the parameter image data is set on the parameter image data. In step S10 of FIG. 7, the parameter image data and the ultrasonic image data at the diastolic heartbeat time phase closest to the desired diastolic heartbeat time phase set by the input unit 13 are extracted from the plural time-series parameter image data and the plural time-series ultrasonic image data and then are displayed on the monitor 122 of the display unit 12.

According to the second embodiment of the invention, by observing the parameter image data based on the motion parameter of the myocardial tissue acquired by analyzing the ultrasonic image data collected in advance, it is possible to accurately and reliably display the parameter image data at the diastolic heartbeat time phase closest to the desired diastolic heartbeat time phase effective for diagnosis. Accordingly, it is possible to improve the diagnosis efficiency and the diagnosis precision and to reduce the operator's burden.

Particularly, in this embodiment, similarly to the first embodiment, since the systole end of the myocardial tissue is specified on the basis of the ultrasonic image data in which the cardiac cavity area is the minimum and which are selected from the time-series ultrasonic image data, it is possible to accurately set the desired diastolic heartbeat time phase based on the systole end without depending on the detection of the T wave in the electrocardiographic waveform. In addition, since the desired diastolic heartbeat time phase is set by the % heartbeat time phase based on the diastole, it is possible to easily set the heartbeat time phase effective for diagnosis even when the heartbeat period varies person by person.

According to the second embodiment, since the parameter image data can be generated and displayed on the basis of the time-series ultrasonic image data supplied from an independent ultrasonic diagnosis device through a network and the like, the operator can efficiently diagnose the sample without any constraint of time or space.

Although the embodiments of the invention are described hitherto, the invention is not limited to the embodiments, but may be modified in various forms. For example, in the above-mentioned embodiments, the time-series parameter image data in which the diastolic heartbeat time phase is set are generated using the time-series ultrasonic image data stored in advance in the ultrasonic image data storage unit 5 or the ultrasonic image data storage unit 16, one parameter image data at the diastolic heartbeat time phase Px closest to the desired diastolic heartbeat time phase Pxo is selected from the generated parameter image data, and then the selected parameter image data is displayed as an still image. However, the parameter image data at the diastolic heartbeat time phase Px may be selected over plural heartbeat periods and the selected parameter image data may be continuously displayed, or may be displayed while being updated by the use of the display mode converters 132-c shown in FIG. 4.

The period Ts of the systole and the period Ts from the systole end to the desired heartbeat time phase Px may be set in advance by the use of the heartbeat period setting unit 7 and the heartbeat time phase setting unit 132 and then the parameter image data at the diastolic heartbeat time phase Px may be generated on the basis of the ultrasonic image data supplied from the ultrasonic image data generating unit 4 or the independent ultrasonic diagnosis device in a predetermined time T0 (T0≈Ts+Tx) after the R-wave generating timing in the electrocardiographic waveform. According to this method, the parameter image data at the diastolic heartbeat time phase Px can be displayed in real time in the unit of heartbeat period and for example, the temporal variation of the myocardial tissue of the sample before or after the motion load or before or after the medicine load can be accurately observed.

Although it has been described in the above-mentioned embodiments that the "strain" of the myocardial tissue is measured as the motion parameter, "displacement", "rotation", "torsion", and "velocity" may be measured as the motion parameter, or "strain rate", "rotation rate", "torsion rate", and "acceleration" indicating the temporal variation of the physical quantities may be measured.

Although it has been described that the ultrasonic image data acquired at the generation timing of the R wave in the electrocardiographic waveform is set as the reference ultrasonic image data used for initially setting the inner cardiac membrane and the outer cardiac membrane, the ultrasonic image data acquired at any heartbeat time phase may be set as the reference ultrasonic image data.

On the other hand, the ultrasonic image data generated by the ultrasonic image data generating unit 4 are not limited to the B-mode image data, but may be other ultrasonic image data such as color Doppler image data or TDI image data. The ultrasonic image data may be generated three-dimensionally.

In the above-mentioned embodiments, the desired heartbeat time phase Pxo is set at the time point when the time-series parameter image data are generated by the parameter image data generating unit 10 (step S9 of FIG. 5 or 7), but the desired heartbeat time phase Pxo may be set at the initial setting process of step S1.

On the other hand, in the above-mentioned embodiments, the parameter image data and the ultrasonic image data are synthesized and displayed, but they may be displayed in parallel or only the parameter image data may be displayed. Alternatively, the parameter image data at plural desired heartbeat time phases Px generated under different photographing conditions like before and after the motion load or before and after the medicine load may be displayed in parallel.

Although it has been described that the systole end of the myocardial tissue is specified by the ultrasonic image data having the minimum cardiac cavity area, the systole end may be specified on the basis of the closing timing of the aortic valve observed from the ultrasonic image data. When the T wave can be easily observed in the electrocardiographic waveform, the systole end may be specified on the basis of the T-wave generating timing.

In the above-mentioned embodiment, the tracking process is performed on the ultrasonic image data acquired by the algebraic conversion of the algebraic converter 42 of the ultrasonic image data generating unit 4 to measure various motion parameters, but the invention is not limited to the configuration. The tracking process may be performed on the received signals output from the adder 224 of the receiver unit 22 or the output signal of the envelope detector 41.

Although it has been described that the diastolic heartbeat time phases P1 to PM are set on the parameter image data E1 to EM generated by the parameter image data generating unit 10 and the parameter image data Ex having the diastolic heartbeat time phase Px closest to the desired heartbeat time phase Pxo are extracted, the parameter image data Ex may be generated directly on the basis of the ultrasonic image data Dx at the diastolic heartbeat time phase Px closest to the desired heartbeat time phase Pxo.

The measurement of the cardiac cavity area, the setting of the diastole and the systole of the myocardial tissue, the setting of the diastolic heartbeat time phase, the measurement of the motion parameter of the myocardial tissue, the generation of the parameter image data, and the extraction of the parameter image data at the diastolic heartbeat time phase closest to the desired heartbeat time phase, which are performed by the units such as the cavity area measuring unit 6, the heartbeat period setting unit 7, the time phase setting unit 8, the motion parameter measuring unit 9, the parameter image data generating unit 10, and the image data extracting unit 11 shown in FIG. 1 or 6, may be carried out by hardware, but all or a part thereof may be generally carried out by software.

What is claimed is:

1. An ultrasonic diagnosis device for measuring a motion parameter of a biological tissue on the basis of time-series ultrasonic image data collected by ultrasonic scanning on a sample and generating parameter image data on the basis of the motion parameter, the ultrasonic diagnosis device comprising:
 a motion parameter measuring unit measuring a motion parameter of the biological tissue on the basis of the ultrasonic image data;
 a parameter image data generating unit generating time-series parameter image data on the basis of the motion parameter;
 a heartbeat period setting unit setting the diastole and the systole of the biological tissue;
 a time phase setting unit setting a diastolic heartbeat time phase relative to the systole end of the biological tissue on the respective time-series parameter image data at least in the diastole of the ultrasonic image data;
 a heartbeat time phase setting unit setting a desired heartbeat time phase based on a ratio to the diastole;
 an image data extracting unit extracting the parameter image data at the diastolic heartbeat time phase corresponding to the desired heartbeat time phase; and
 a display unit displaying the extracted parameter image data.

2. The ultrasonic diagnosis device according to claim 1, wherein the motion parameter measuring unit sets a plurality of sampling points on the biological tissue in the ultrasonic image data and measures the motion parameter of the biological tissue by performing a tracking process using pattern matching based on the sampling points.

3. The ultrasonic diagnosis device according to claim 1, wherein the motion parameter measuring unit measures as the motion parameter at least one of strain, displacement, rotation, torsion, velocity, strain rate, rotation rate, torsion rate, and acceleration of the biological tissue.

4. The ultrasonic diagnosis device according to claim 1, further comprising:
 a cavity area measuring unit measuring a cavity area of the biological tissue in the ultrasonic image data; and
 an ECG measuring unit measuring an electrocardiographic waveform of the sample,
 wherein the heartbeat period setting unit sets the diastole and the systole of the biological tissue on the basis of the systole end specified by the ultrasonic image data in which the cavity area of the biological tissue that is measured by the cavity area measuring unit and the diastole end specified by R-wave timing information of the electrocardiographic waveform that is measured by the ECG measuring unit.

5. The ultrasonic diagnosis device according to claim 1, further comprising an ECG measuring unit measuring an electrocardiographic waveform of the sample,
 wherein the heartbeat period setting unit sets the diastole and the systole of the biological tissue on the basis of R-wave timing information and T-wave timing information of the electrocardiographic waveform measured by the ECG measuring unit.

6. The ultrasonic diagnosis device according to claim 1, further comprising:
 a timing specifying unit specifying the closing timing of an aortic valve in the ultrasonic image data; and
 an ECG measuring unit measuring an electrocardiographic waveform of the sample,
 wherein the heartbeat period setting unit sets the diastole and the systole of the biological tissue on the basis of the systole end specified by the closing timing information from the timing specifying unit and the diastole end specified by R-wave timing information of the electrocardiographic waveform measured by the ECG measuring unit.

7. The ultrasonic diagnosis device according to claim 1, wherein the time phase setting unit sets the heartbeat time phase of the diastole that is expressed in a ratio (%) based on a period from the systole end to the diastole end subsequent to the systole end.

8. The ultrasonic diagnosis device according to claim 1, wherein the image data extracting unit extracts the ultrasonic image data in which the diastolic heartbeat time phase is set along with the parameter image data, and
 wherein the display unit synthesizes or puts in a line and displays the parameter image data and the ultrasonic image data.

9. The ultrasonic diagnosis device according to claim 1, wherein the image data extracting unit extracts the parameter image data in which the diastolic heartbeat time phase closest to the desired heartbeat time phase that is set by the heartbeat time phase setting unit.

10. The ultrasonic diagnosis device according to claim 1, wherein the display unit displays in a line the parameter image data at a plurality of the desired heartbeat time phases generated under different photographing conditions.

11. The ultrasonic diagnosis device according to claim 1, wherein the time phase setting unit sets a time point in T/3 after the systole end as the diastolic heartbeat time phase on the basis of a period T from the systole end to the diastole end subsequent to the systole end.

12. The ultrasonic diagnosis device according to claim 1, wherein the time phase setting unit sets a time point in 0.30T to 0.34T after the systole end as the diastolic heartbeat time phase on the basis of a period T from the systole end to the diastole end subsequent to the systole end.

13. The ultrasonic diagnosis device according to claim 1, wherein the display unit segments the biological tissue in accordance with a predetermined criterion, averages values of the motion parameter every segment obtained by the segmentation, and displays the averaged value of the motion parameter as the parameter image data.

14. An ultrasonic image analysis device comprising:
 an ultrasonic image data storage unit storing time-series ultrasonic image data collected by ultrasonic scanning on a sample;
 a motion parameter measuring unit measuring a motion parameter of a biological tissue on the basis of the ultrasonic image data;
 a parameter image data generating unit generating time-series parameter image data on the basis of the motion parameter;
 a heartbeat period setting unit setting the diastole and the systole of the biological tissue;
 a time phase setting unit setting a diastolic heartbeat time phase relative to the systole end of the biological tissue on the respective time-series parameter image data at least in the diastole of the ultrasonic image data;
 a heartbeat time phase setting unit setting a desired heartbeat time phase based on a ratio to the diastole;
 an image data extracting unit extracting the parameter image data at the diastolic heartbeat time phase corresponding to the desired heartbeat time phase; and a display unit displaying the extracted parameter image data.

15. The ultrasonic image analysis device according to claim 14, wherein the motion parameter measuring unit sets a plurality of sampling points on the biological tissue in the ultrasonic image data and measures the motion parameter of the biological tissue by performing a tracking process using pattern matching based on the sampling points.

16. The ultrasonic image analysis device according to claim 14, wherein the motion parameter measuring unit measures as the motion parameter at least one of strain, displacement, rotation, torsion, velocity, strain rate, rotation rate, torsion rate, and acceleration of the biological tissue.

17. The ultrasonic image analysis device according to claim 14, further comprising:
a cavity area measuring unit measuring a cavity area of the biological tissue in the ultrasonic image data; and
an ECG measuring unit measuring an electrocardiographic waveform of the sample,
wherein the heartbeat period setting unit sets the diastole and the systole of the biological tissue on the basis of the systole end specified by the ultrasonic image data in which the cavity area of the biological tissue that is measured by the cavity area measuring unit is the smallest and the diastole end specified by R-wave timing information of the electrocardiographic waveform that is measured by the ECG measuring unit.

18. The ultrasonic image analysis device according to claim 14, further comprising an ECG measuring unit measuring an electrocardiographic waveform of the sample,
wherein the heartbeat period setting unit sets the diastole and the systole of the biological tissue on the basis of R-wave timing information and T-wave timing information of the electrocardiographic waveform measured by the ECG measuring unit.

19. The ultrasonic image analysis device according to claim 14, further comprising:
a timing specifying unit specifying the closing timing of an aortic valve in the ultrasonic image data; and
an ECG measuring unit measuring an electrocardiographic waveform of the sample,
wherein the heartbeat period setting unit sets the diastole and the systole of the biological tissue on the basis of the systole end specified by the closing timing information from the timing specifying unit and the diastole end specified by R-wave timing information of the electrocardiographic waveform measured by the ECG measuring unit.

20. The ultrasonic image analysis device according to claim 14, wherein the time phase setting unit sets the heartbeat time phase of the diastole that is expressed in a ratio (%) based on a period from the systole end to the diastole end subsequent to the systole end.

21. The ultrasonic image analysis device according to claim 14, wherein the image data extracting unit extracts the ultrasonic image data in which the diastolic heartbeat time phase is set along with the parameter image data, and
wherein the display unit synthesizes or puts in a line and displays the parameter image data and the ultrasonic image data.

22. The ultrasonic image analysis device according to claim 14, wherein the image data extracting unit extracts the parameter image data in which the diastolic heartbeat time phase closest to the desired heartbeat time phase that is set by the heartbeat time phase setting unit.

23. The ultrasonic image analysis device according to claim 14, wherein the display unit displays in a line the parameter image data at a plurality of the desired heartbeat time phases generated under different photographing conditions.

24. The ultrasonic image analysis device according to claim 14, wherein the time phase setting unit sets a time point in T/3 after the systole end as the diastolic heartbeat time phase on the basis of a period T from the systole end to the diastole end subsequent to the systole end.

25. The ultrasonic image analysis device according to claim 14, wherein the time phase setting unit sets a time point in 0.30T to 0.34T after the systole end as the diastolic heartbeat time phase on the basis of a period T from the systole end to the diastole end subsequent to the systole end.

26. The ultrasonic image analysis device according to claim 14, wherein the display unit segments the biological tissue in accordance with a predetermined criterion, averages values of the motion parameter every segment obtained by the segmentation, and displays the averaged value of the motion parameter as the parameter image data.

27. An ultrasonic image analysis method comprising:
ultrasonic scanning, by an ultrasonic scanning apparatus, a sample;
measuring a motion parameter of a biological tissue on the basis of time-series ultrasonic image data collected by the ultrasonic scanning on the sample;
generating time-series parameter image data on the basis of the motion parameter;
setting the diastole and the systole of the biological tissue;
setting a diastolic heartbeat time phase relative to the systole end of the biological tissue on the respective time-series parameter image data at least in the diastole of the ultrasonic image data;
setting a desired heartbeat time phase based on a ratio to the diastole;
extracting the parameter image data at the diastolic heartbeat time phase corresponding to the desired heartbeat time phase; and
displaying the extracted parameter image data.

* * * * *